(12) United States Patent
Fogelman et al.

(10) Patent No.: US 10,279,294 B2
(45) Date of Patent: May 7, 2019

(54) SELF CLEANING GAS-LIQUID SEPARATOR FOR SERIAL OR PARALLEL COLLECTION OF LIQUID FRACTIONS

(75) Inventors: Kimber D Fogelman, Hockessen, DE (US); Terry A Berger, Englewood, FL (US); Edwin E Wikfors, Landenberg, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 995 days.

(21) Appl. No.: 14/123,191

(22) PCT Filed: Jun. 1, 2012

(86) PCT No.: PCT/US2012/040584
§ 371 (c)(1),
(2), (4) Date: Jun. 4, 2014

(87) PCT Pub. No.: WO2012/167180
PCT Pub. Date: Dec. 6, 2012

(65) Prior Publication Data
US 2014/0283688 A1    Sep. 25, 2014

Related U.S. Application Data

(60) Provisional application No. 61/492,352, filed on Jun. 1, 2011.

(51) Int. Cl.
*B01D 46/00* (2006.01)
*B01D 11/02* (2006.01)
(Continued)

(52) U.S. Cl.
CPC ...... *B01D 46/0031* (2013.01); *B01D 11/0203* (2013.01); *B01D 11/0292* (2013.01);
(Continued)

(58) Field of Classification Search
CPC .. B01D 46/00; B01D 46/003; B01D 46/0031; B01D 46/0082; B01D 46/0067;
(Continued)

(56) References Cited

U.S. PATENT DOCUMENTS 4,359,329 A    11/1982  Willeitner
4,487,618 A *  12/1984  Mann ................. B01D 46/0012
                                                         55/323
(Continued)

FOREIGN PATENT DOCUMENTS

CN        1717273        1/2006
JP     2007120972 A       5/2007
(Continued)

OTHER PUBLICATIONS

Office Action dated Dec. 25, 2014 in CN Application No. 201280026910.6 (Unofficial/Non-certified translation by provided foreign agent included).
(Continued)

*Primary Examiner* — T. Bennett McKenzie (57) ABSTRACT

An apparatus, process, and system are disclosed that effectively provide separation of a combined gas/liquid flow stream into its separated gas and liquid factions. The invention is primarily directed to the fields of preparative supercritical fluid chromatography (SFC) and supercritical fluid extraction (SFE), but will have other utilization and applicability where phases of dramatically different density, viscosity and volumetric flow require separation.

17 Claims, 9 Drawing Sheets

(51) Int. Cl.
*B01D 11/04* (2006.01)
*B01D 15/24* (2006.01)
*B01D 15/40* (2006.01)
*G01N 30/80* (2006.01)
*G01N 30/84* (2006.01)

(52) U.S. Cl.
CPC ........ *B01D 11/0407* (2013.01); *B01D 46/003* (2013.01); *B01D 46/0082* (2013.01); *B01D 15/247* (2013.01); *B01D 15/40* (2013.01); *G01N 30/80* (2013.01); *G01N 30/84* (2013.01); *G01N 2030/8411* (2013.01)

(58) Field of Classification Search
CPC ............ B01D 11/0203; B01D 11/0292; B01D 11/0407; B01D 15/247; B01D 15/40; G01N 30/80; G01N 30/84; G01N 2030/8411
USPC ................ 95/273, 281; 55/423, 495; 96/233
See application file for complete search history.

(56) References Cited

U.S. PATENT DOCUMENTS

| | | | |
|---|---|---|---|
| 5,439,494 A * | 8/1995 | Tullis | B01D 46/003 55/283 |
| 5,846,271 A | 12/1998 | Flynn et al. | |
| 5,919,284 A | 7/1999 | Perry, Jr. et al. | |
| 6,485,535 B1 * | 11/2002 | Linnersten | B01D 46/0004 55/319 |
| 8,327,725 B2 | 12/2012 | Kanomata | |
| 2004/0065110 A1 | 4/2004 | Barratt et al. | |
| 2007/0062595 A1 * | 3/2007 | Bhatnagar | B32B 1/08 138/125 |
| 2008/0245037 A1 * | 10/2008 | Rogers | B01D 39/163 55/385.3 |
| 2008/0276580 A1 * | 11/2008 | Knauf | F01M 11/0408 55/290 |
| 2011/0056379 A1 | 3/2011 | Lucas | |
| 2011/0315018 A1 * | 12/2011 | Moens | B01D 46/0004 96/400 |

FOREIGN PATENT DOCUMENTS

WO   2007093690 A1   8/2007
WO   WO 2007093690 A1 *   8/2007   ............... B01D 1/16

OTHER PUBLICATIONS

Machine Translation of CN1717273.
Machine Translation of JP2007120972A.
International Search Report and Written Opinion dated Dec. 28, 2012 in International Application No. PCT/US2012/040584.
Extended European Search Report dated Jan. 29, 2016 from related European Application No. 12793285.3.

* cited by examiner

SELF CLEANING GAS-LIQUID SEPARATOR FOR SERIAL OR PARALLEL COLLECTION OF LIQUID FRACTIONS

The present application is a National Stage application under 35 U.S.C. § 365 of International Patent Application No. PCT/US2012/040584 filed on Jun. 1, 2012 naming Kimber Fogelman, et al. as inventors. Priority is claimed from International Patent Application No. PCT/US2012/040584 and from U.S. Provisional Application No. 61/492,352 filed on Jun. 1, 2011. The entire disclosures of International Patent Application No. PCT/US2012/040584 and U.S. Provisional Application No. 61/492,352 are specifically incorporated herein by reference.

FIELD OF THE DISCLOSURE

The present invention generally relates to technical fields of supercritical fluid chromatography and supercritical fluid extraction but includes alternative utilization and applications where phases of dramatically different density, viscosity, and volumetric flow require separation.

BACKGROUND

Supercritical fluid extraction (SFE) and preparative ("Prep") supercritical fluid chromatography (SFC) each require devices and processes for collecting liquid fractions from the terminus of the flow system. The major components of supercritical fluid (SF) mobile phases include highly pressurized gas such as carbon dioxide (CO2, or $CO_2$) and liquid organic co-solvents, or modifiers. For collection, the mobile phase must be brought to near ambient pressure where the CO2 component is an expanded gas with up to 500 times the volume of the pressurized phase. A much smaller volume of residual liquid modifier containing the compounds of interest is entrained with the CO2, initially as an aerosol. As a result, the process of collecting the compounds of interest is more complicated than fraction collection in Preparative High Performance Liquid Chromatography (HPLC) where only liquids are used. The collection process in either Prep SFC or SFE involves several steps including: a) depressurization of the mobile phase; b) optional heating to restore heat of evaporation of the evaporating CO2 phase; c) partitioning of the resulting gas and liquid phases d) venting of the vapor and e) direction of the residual liquid phase to a suitable collection container.

Depressurization of the mobile phase is initiated when the mobile phase passes through a back pressure regulator (BPR), which is usually set to a control setpoint of 100 bar or greater to maintain ideal chromatographic/extraction conditions. Flow continues beyond the BPR in a very chaotic state of evaporating liquid CO2 and expanding vapor CO2. Such extreme turbulence within this flow region tends to aerosolize much of the residual organic liquid from the mobile phase. In addition, the evaporating CO2 causes considerable cooling of the residual liquid organic which allows it to retain a high concentration of dissolved CO2.

Flow is generally delivered via a transfer line from the BPR to a gas-liquid separator. The general role of the gas-liquid separator is to complete the expansion of the CO2 vapor to a designated pressure, and allow venting of the vapor while simultaneously collecting the residual liquid or redirecting it along a selected path to a collection container. In order to accomplish this task some method must be used to handle residual aerosols emerging from the flow transfer line. Since the degree of aerosolization depends upon both flow rate and composition of the mobile phase, the gas-liquid separator must be sized to handle appropriate ranges for both parameters.

Figure 9:
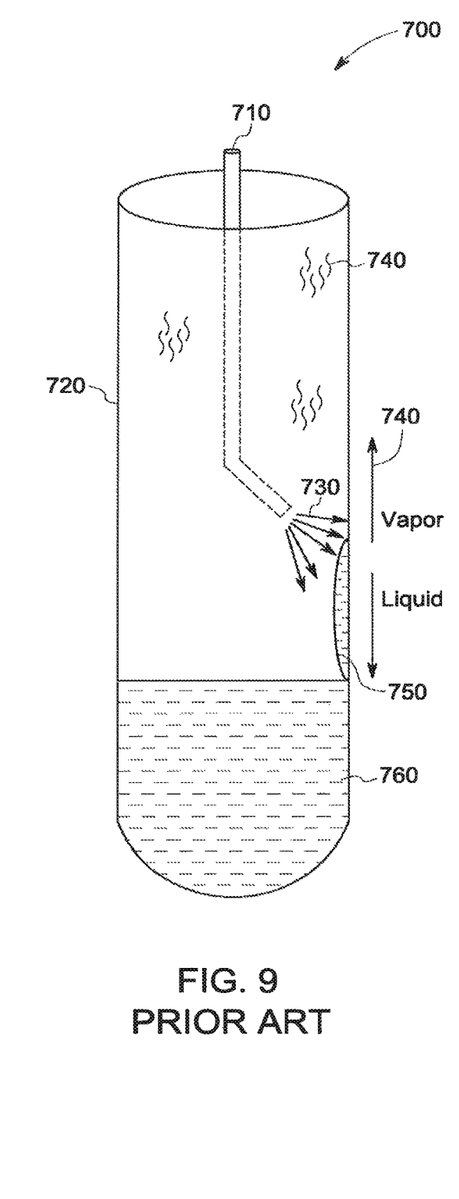
FIG. 9 illustrates a separation and collection design of the prior art.

Several techniques and devices for aerosol suppression in gas-liquid separators are known in the industry. FIG. 9 illustrates such a device 700 where the flow line 710 can be introduced into an open top-end of separator 720 in such a manner that the liquid aerosol 730 collides with the separator wall and coalesces to a film 750 which drains by gravity down the wall. Not shown is a multi-step heater assembly to condition the flow to separate the gas and liquid phases and dramatically suppress aerosol in the transfer tubing. The CO2 and any organic vapor 740 are allowed to vent out the top of the separator by pneumatic forces. It is known to hold the internal pressure of the separator at an elevated pressure in order to slow the velocity of the aerosol 730 escaping from narrow flow line 710. This has the effect of reducing the shear forces that might lift the coalesced liquid 760 upward on the wall or re-aerosolize the liquid film 750.

Figure 10:
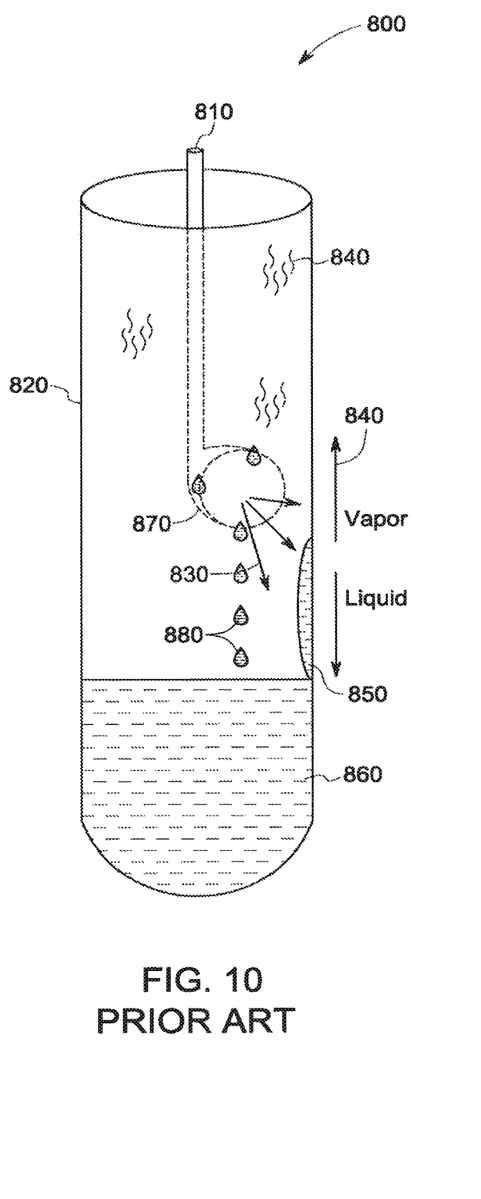
FIG. 10 illustrates another separation and collection design of the prior art.

FIG. 10 illustrates another device 800 often used to slow gaseous flowstream (e.g. CO2) velocity by adjusting the internal diameter of the transfer line as it enters the separator. Flow line 810 can be introduced into an open top-end of separator 820 in such a manner that the liquid aerosol 830 collides with the separator wall and coalesces to a film 850 which drains by gravity down a wall. The CO2 and any organic vapor are allowed to vent 840 out the top of the separator by pneumatic forces. It is known to hold the internal pressure of the separator 800 at an elevated pressure in order to slow further the velocity of the aerosol 830. This has the effect of reducing the shear forces that might lift the coalesced liquid 860 upward on the wall or re-aerosolize the liquid film 850. The exit end 870 of transfer line 810 into separator 800 has an enlarged diameter that is some multiple of a normal diameter of tube 810. For example, by doubling the internal diameter (i.d.) of a round tube, the flow velocity is cut to 25% of its original velocity.

Regardless of the suppression type, most separators experience some level of fouling from liquid droplets 880 reaching poorly swept regions of the internal surface of the separator. This is problematic when the same separator must be used for different samples since it introduces a carryover or cross-contamination issue that destroys the integrity of subsequent collectable fractions into the separator. As a result, a manual or automated cleaning process is typically required to prepare the separator for the next fraction type. Generally this is accomplished by solvent rinsing of the reused parts of the collector. In one case use of a replaceable collection liner (e.g. test tube) removes the fouled surfaces with the collected fraction.

In either Prep SFC or SFE, mobile phase exiting the instrument is frequently enriched with dissolved compounds of interest that require collection. A flow segment containing either an individual or a group of such compounds and properly directed to a known container is called a fraction. Fractions may also be flow segments delivered out of the instrument in a given time window, whether they contain dissolved compounds or not. The apparatus that delivers different fractions to separate containers is called a fraction collector assembly. Gas-liquid separators are part of the fraction collector assembly in Prep SFC and SFE systems and are generally designed either for parallel or serial collection use. In a parallel configuration, an individual collector comprises a single gas/liquid separator in series with a single collection container. Frequently, the collection container itself is integral to the gas/liquid separator apparatus to form the collector. At other times the collection container is remote from the separator but dedicated to exclusively receiving its fractions. Individual collectors are then plumbed in multiple parallel collection paths depending on the maximum number of distinct fractions to be collected per separation. The individual path to a specific collector is generally determined by a valving arrangement which is also part of the fraction collector assembly. Parallel fraction collector assemblies typically collect a single chromatographically separated fraction in each collector for each separation. Multiple separations may pool identical fractions from separate separations into the same collector to enable collection of larger amounts of the compounds of interest. Regardless, each gas-liquid separator contacts only one type of fraction. Hence, there is no need for cleaning of the separator until all like fractions have been collected.

In a series gas-liquid separator arrangement, a single gas/liquid separator delivers the liquid portion of fractions to more than one collection container. As a result, more than one type of sample fraction flows through the separator for a given separation. Separators of this type are flow through and do not incorporate a single collection container as a permanent part of the collector. Instead, multiple collection containers are attachable to the separator exit port typically via a transfer line using a robotic or valving assembly to switch to each targeted collection container. This type of separator must be designed to clear each fraction rapidly and rinse itself, prior to the next fraction entering the separator. Also, the design must take into account not only the gas-liquid separation process, but the drain rate of the liquid to the separator's exit port that is typically located near the bottom of the separator. In addition, sufficient rinsing must be applied and cleared from the separator to minimize cross-contamination between fractions. Series gas-liquid separators can operate in a continuous manner or as an array of two or more separators that alternate to allow for both collecting and rinsing functions. They generally have much lower internal surface area than parallel separators in order to limit un-swept areas and minimize rinse volumes.

Limiting the drain time and avoiding excess surface area contact are critical in the design of such separators. Surfaces which coalesce the liquid fractions must be clean and allow free-flowing of the droplets to the collector exit port in as a little time as possible. Most prior collectors have the drawback that drain times vary considerably depending on the liquid composition of the mobile phase. Further, changing the chemical nature of the organic liquid phase for example from one of low viscosity to one of high viscosity can dramatically affect the drain time.

Given the constraints for series separators, it is not surprising to find their useful dynamic range significantly limited. For example, a commercial series separator currently available fixes the total flow rate of the mobile phase and maintains a constant level of a single type of organic liquid into the separator using a makeup pump. The inability to optimize flow rate and select various modifier solvents for the chromatographic separation represents a severe limitation of the system.

Additionally, both parallel and serial gas-liquid separators are subject internal pressurization. This places a constraint on the materials that can be used to construct the separator. For many high-pressure applications, metal cyclones are generally required. For lower pressure applications, however, it is often desirable to use transparent materials for the separator such as glass. Glass material places a practical upper limit on the amount of pressurization that can be safely achieved without breaking or exploding the separator. For example, as a safety factor a glass separator must generally be shielded in the event of over-pressurization.

What is clearly needed is a simplified, low pressure gas-liquid separator that can be used in either a parallel or serial collection configuration. The separator configurations should be self-cleaning without manual or significant manual intervention and promote a high degree of recovery of the liquid phase to maximize solute-of-interest recovery.

SUMMARY

The various embodiments described as devices, systems, and methods of the present invention provide designs and techniques that solve many of the problems of existing gas-liquid separation technology. The embodiments provide a continuously self-cleaning flowpath which minimizes the potential for cross-contamination carryover with minimal or no manual rinsing. In addition, features of the present invention allow collection very near to atmospheric pressure, which provides the advantages that both large and small containers may be used for solute or sample fraction collection while reducing the safety risk of over-pressurization. The embodiments may also be used or operated in either a parallel or serial configuration or steps for collection.

Components and operation of the present embodiments for a gas-liquid separator include using a porous metal or polymeric woven fiber filter, or porous ceramic which receives a gas-liquid flow stream via an inlet tube. Preferably, the entire flow stream is forced by upstream pneumatic and hydraulic pressures through the filter. Aerosol droplets from the flowstream contact the large surface area of the porous filter wall and tend to coalesce and form larger droplets.

Expanding $CO_2$ and organic vapors ensure a rapid delivery of the coalesced liquid through the filter wall. The external surface area of the filter is generally sized to be several orders of magnitude greater than the cross sectional area of the inlet tube delivering the gas-liquid flow stream into the filter. As a result, the linear velocity of the separated gas and vapors is reduced proportionately. The combination of lower gas velocity and larger droplet size prevents re-aerosolization of the liquid phase.

In some embodiments, the external surface of the filter is physically constrained by a type of housing. An exemplary radial constraint, for example, takes the form of a spiral channel having an inner diameter that matches or nearly matches an outer diameter of an exemplary cylindrical filter. The spiral path is sealed at the upper end to prevent vapor flow out of the filter from escaping out of the top. As a result, gas, vapor, and liquid are forced downward through the spiral channel as the separated flowstreams emerge from the filter.

The spiral channel can be created in several ways. For example, the filter can be forced into a polymeric convoluted tube with an appropriate inner diameter. The tube is generally cut to a length slightly longer than the bottom of the filter. Hence, while the liquid will tend to continue its path along the spiral channel, the vapor is free to further expand once it is no longer constrained by the filter element and channel. In a similar manner, the channel can be created by machining an oversized metal tube and pressing in the filter.

A clear design advantage is realized by having the spiral channel continue after the bottom of the filter. That is, the vast majority of liquid continues to follow the channel and emerges at a single point of the separator circumference. The focusing of liquid flow at one point of the separator bottom rather than at random locations dramatically reduces both the volume of vapor contact of the liquid droplets since the vapor is free to escape across the entire cross section and the number of unswept droplets that could otherwise form at various locations on the separator's bottom circumference. Further; the channel end can actually be shaped to a spout or drip edge to ensure droplets release in a reasonable volume range.

The exemplary separator designs solve several problems mentioned above. First, the final pressure barrier necessary to expand the CO2 vapor to atmospheric pressure is when the flowstream passes through the filter. Since filters can be fabricated to contain fairly high internal pressure, a single filter can handle a wide dynamic range of flows. Additionally, since gas and vapor velocity is greatly attenuated by the larger filter's large external surface and the channel cross section, the external container of the separator does not have to be pressurized in order to reduce the velocity further. Second, the liquid is delivered with some radial pneumatic force into the constraining channel, which represents a well-swept and relatively small surface on which cross-contamination might occur. Third, the liquid is delivered in a downward direction at moderate velocity, which minimizes the time required to reach the exit port of the separation apparatus. Use of the separator may occur within the mouth of a single collection container or in a flow-through container that directs the separated liquid to one of many collection containers via an exit port and transfer line.

Alternative embodiments to the designs and methods of the preferred embodiments including making the bottom or lower regions of the filter impermeable in order to force gas and liquid components of the flowstream to escape radially out of a cylindrical filter. In one embodiment, a downward draft of inert vapor can be supplied into the top of the spiral channel to push liquid trapped in the upper region of the assembly towards the bottom end of the separator. A drip line can be affixed to the channel exit to guide the liquid droplets to a specific location in the separator. This location can be directly to the exit port and on to a series of collection containers. Such a feature minimizes any splashing of airborne droplets falling from the separator element. Further, a makeup solvent flow can be added either before or after the BPR in order to assure a minimum of liquid phase reaching the separator. To clean the separator assembly, a surge of wash solvent may be applied in between fraction collectors using a secondary wash pump or an injection valve. This cleaning operation further eliminates cross-contamination with subsequent injection runs.

BRIEF DESCRIPTION OF THE FIGURES

The accompanying figures where like reference numerals refer to identical or functionally similar elements throughout the separate views and which together with the detailed description below are incorporated in and form part of the specification, serve to further illustrate various embodiments and to explain various principles and advantages.

DETAILED DESCRIPTION

In the following description of preferred and alternative embodiments, reference is made to the accompanying drawings which form a part hereof, and in which it is shown by way of illustration specific embodiments in which the invention may be practiced. It is to be understood that other embodiments may be utilized and structural or process changes may be made without departing from the scope of the invention and its preferred and alternative embodiments.

One skilled in the relevant art will recognize that many possible modifications and combinations of the disclosed embodiments can be used, while still employing the same basic underlying mechanisms and methodologies. The descriptions herein, for purposes of explanation, have been written with references to specific embodiments. However, the illustrative discussions within the present application are not intended to be exhaustive or to limit the disclosure to the precise forms disclosed.

Referring to the embodiments illustrated in the figures and process flowcharts, in a high-pressure or supercritical fluid chromatography or extraction process with at least a biphasic flowstream, the embodiments provide a continuously self-cleaning flow path which minimizes the potential for cross-contamination carryover with reduced or no manual rinsing. Further, the embodiments provide collection of liquid separations or fractions at a pressure near to atmospheric. The collection process may be accomplished with collection containers or containers of varying sizes while mitigating or removing safety hazards of over-pressurization during a separation and collection process.

Figure 1:
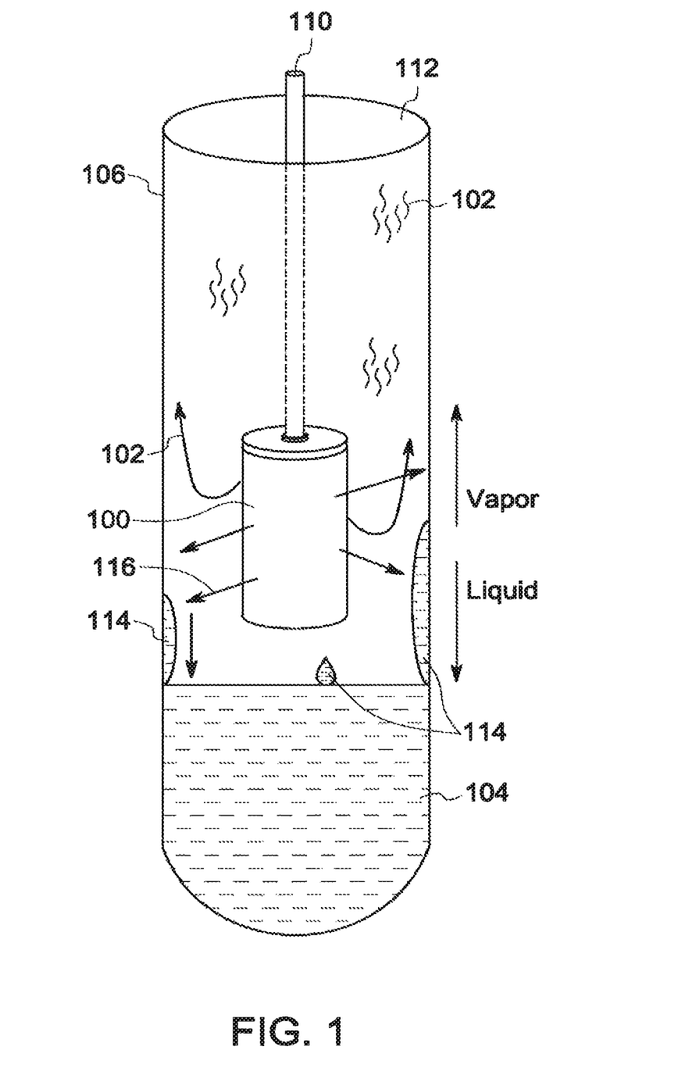
FIG. 1 illustrates an embodiment of a separation filter assembly inserted into a collection tube.
Figure 8:
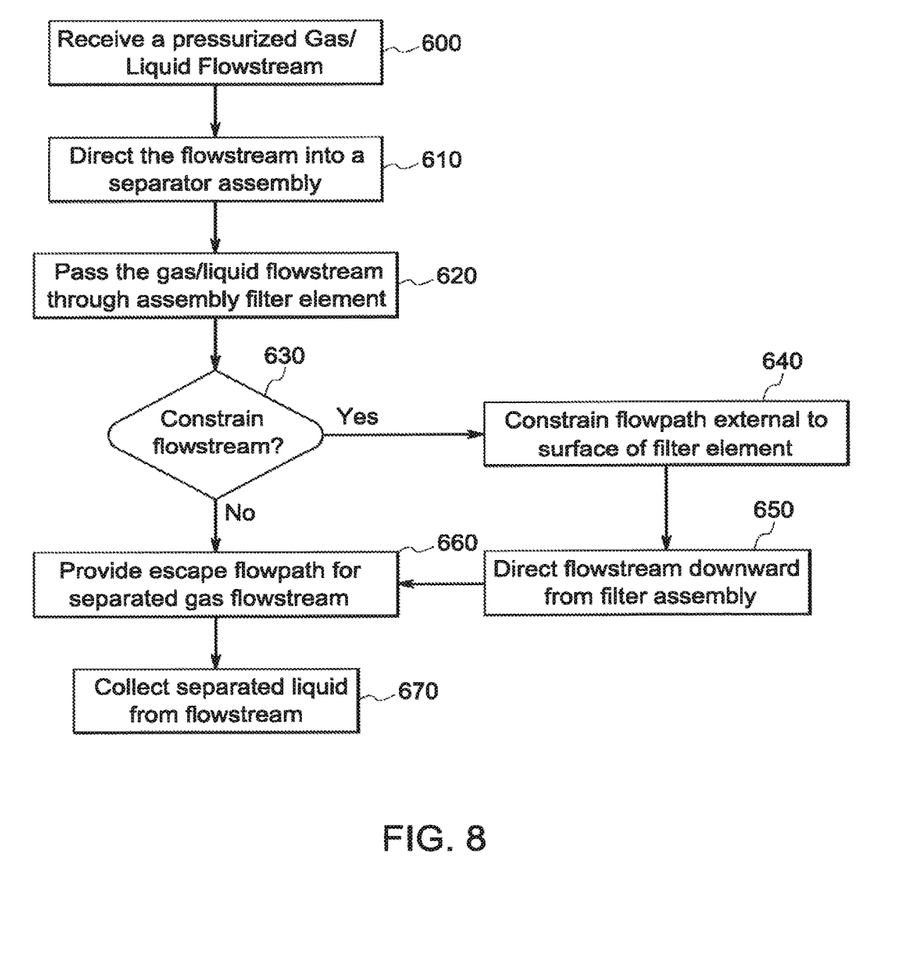
FIG. 8 illustrates an exemplary gas-liquid separation process.

Referring to FIG. 1 and the flowchart of FIG. 8, porous filter 100 with an inlet tube 110 is used as a coalescence filter. Filter 100 is preferably constructed of metal, however alternative materials may be used such as ceramic or a polymer including plastic or resin. However, virtually any porous material that can function as a filter for separation of a gas/liquid flow stream as described herein may be utilized without departing from the scope and spirit of the embodiments. Filter 1 00 may further include a sintered construction that provides for gas and liquid flow through the filter. The external surface area is preferably sized to be one or more orders of magnitude greater than the cross-sectional area of the inlet tube 110 inner diameter, thereby resulting in a proportional reduction in linear velocity of the flowstream. However; the size and shape of the preferred filter element 100 and inlet tube 110 are exemplary and may vary. The scope of the present invention is further intended to cover other possible filter shapes in addition to the exemplary cylindrically-shaped filter 100 illustrated in the figures. During operation, filter 100 is inserted inside a collection container, such as container 106 that is shaped as a test tube. The size and shape of collection container 106 is exemplary and not intended as limiting to the present invention. Other collection container designs or collection processes to collect a liquid flowstream from filter 100 and provide removal of a gas flowstream are anticipated in the various embodiments and do not depart from the scope and spirit of the present invention. During operation, a gas/liquid flowstream mixture is received from a pressurized flowstream 600 entering 610 the internal volume of filter 100 from tube 110, and is passed or forced outward 620 through the tiny random paths of the sintered porous filter element wall, and thereby passes into the interior space of the collection container 106 outside of the filter 100 as depicted by arrows 116. Gaseous or vapor flow 102 may escape 660 through a low pressure escape area 112 which can either be a tube or open area of container 106. The use of an open container presumes the container is located in a well ventilated compartment such as a fume hood to prevent exposure to the escaping vapors. The coalesced liquid droplets 114 may have sufficient momentum to reach the inner wall of container 106 and drain down the inner wall or drip 114 directly from filter 100 toward the collection area. After draining down the container wall or dripping from filter 100, liquid fraction 1 04 collects 670 at the bottom of container 106 by gravity drainage. Alternatively, liquid fraction 104 may be removed from container 106 by positive or negative pressure forces via a drain tube (not shown).

Figure 2:
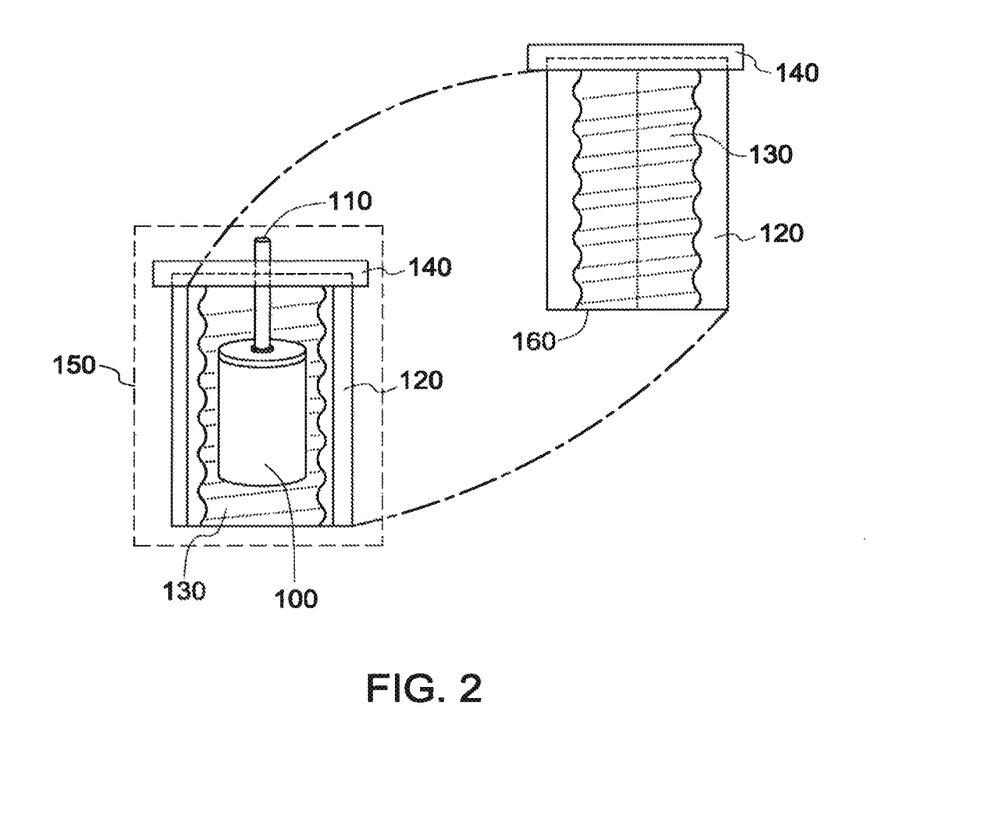
FIG. 2 illustrates an embodiment of a filter assembly with radial constraint.

An additional embodiment of the present invention is illustrated in a filter assembly 150 of FIG. 2, where a constraint 640 has been added to the gas and liquid flowpath. The filter 100 is fitted into a constraint such as exemplary tube 120 having an internal spiral groove 130. The assembly 150 includes a pressure-resistant sealing cap 140 that seals the top of tube 120. The result of this combination is a filter assembly 150 wherein the inlet tube 110 penetrates sealing cap 140 while maintaining a vapor-tight seal. A gas/liquid mixture entering the internal volume of filter 100 is forced outward 620 through the tiny random paths of the sintered porous wall This process affords ample opportunity for small aerosol droplets of the incoming flow stream to combine coalesce and form larger droplets. At the same time, the high velocity gas of the mixed stream is dispersed over the significantly greater surface area of the porous filter and experiences a dramatic reduction in velocity. The combination of lower velocity gas and larger droplet size prevents re-aerosolization of the liquid in the exit stream.

After exiting the external surface of filter 100, emerging liquid and gas are directed or forced 650 into spiral groove 130 of the constraining tube 120. Since sealing cap 140 prevents escape of liquid or gas/vapor from the top of assembly 150, flowstream components are forced downward by both gravity and pneumatic forces. The high flow of vapor sweeping down spiral groove 130 increases the speed of liquid flow over simple gravity drainage and helps to overcome any flow resistance due to surface tension. Hence the spiral groove 130 provides a controlled and well swept surface from which to clear the coalesced liquid. Further the surface of the spiral groove 130 is independent of the collection bottle or separator casing geometry. Spiral groove 130 is also well rinsed by subsequent flow of mobile phase liquid not containing dissolved compounds which gives it the desirable attribute of being self cleaning.

Spiral groove 130 may constructed in several ways including use of a formed tube 120 which may be polymeric as in an extruded convoluted FEP tube. Alternately, a spiral filament such as a spring secured between the two walls of filter 100 and a straight-walled version of tube 120 may be used to create the groove. Another implementation of the groove is metallic as in a stainless steel tube with a machined internal groove. However, other suitable materials and constructions may be used without departing from the scope or spirit of the present invention. A close fit between the filter and the groove internal diameter ensures that the liquid is forced by the emerging vapor stream down the grooved path to bottom portion 160. It is also preferred, but not required, that filter 100 be made impermeable at the top and bottom ends to ensure that the liquid and gas streams are passed directly into the groove rather than dripping out the bottom or top of the filter. Although the embodiments describe a radial constraint around a filter 100, the size, shape, and position of a constraint around filter 100 are exemplary and may vary so long as the flowpath becomes constrained to eventually direct flow in a downward direction from the filter 100 and provide for escape of a gas or vapor in the flow stream and collection of a liquid.

Figure 3:
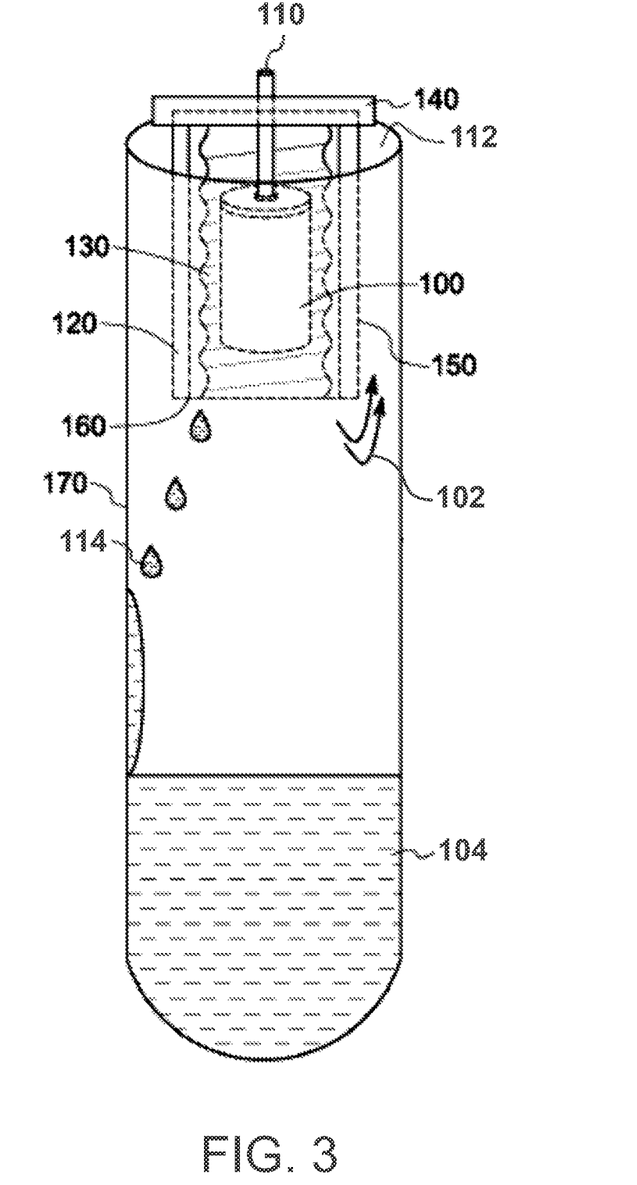
FIG. 3 illustrates an exemplary filter assembly with radial constraint that is inserted into a collection device.
Figure 4:
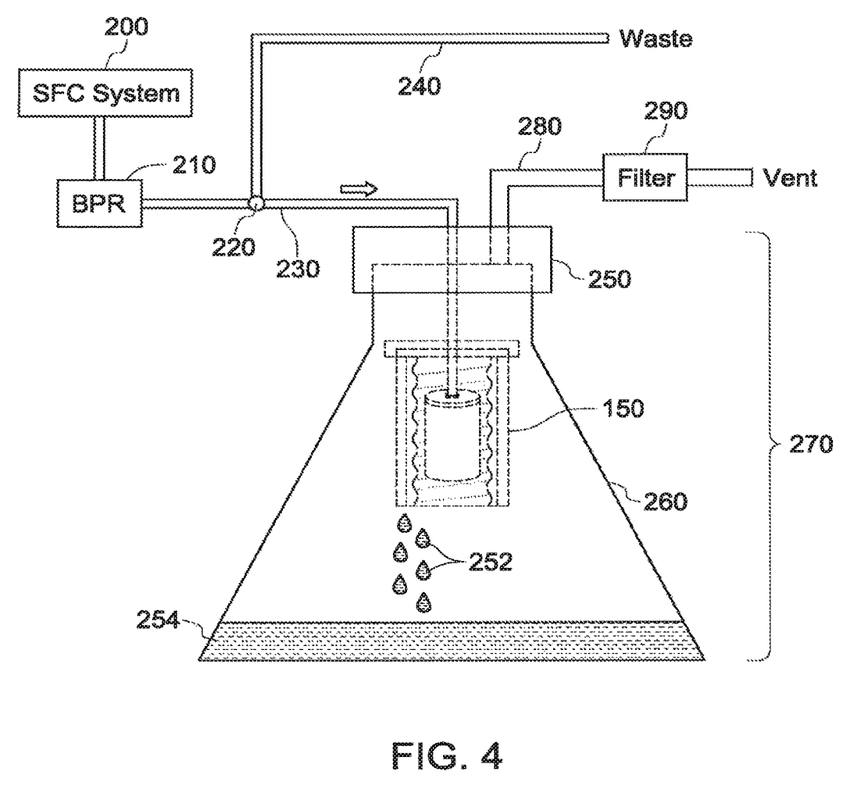
FIG. 4 illustrates an embodiment of a parallel separator system using a preferred filter assembly.

In FIG. 3, filter assembly 150 is illustrated as inserted into an open-top collection container 170. In an exemplary embodiment, container 170 is a collection tube that is relatively larger in diameter than a diameter of cylindrical assembly 150. When a gas-liquid flow stream is introduced at the inlet tube 110, the mixture is already fractionated into its separate phases as an aerosol. As the mixture passes through the wall of filter 100, the tiny aerosol droplets coalesce to larger droplets generally too large to be carried by the rapidly slowing vapor stream. The liquid is continuously forced through the filter wall by pneumatic pressure of the gas. Any small droplets of liquids passing through the filter 100 have an added chance for coalescence within the tortuous path of the spiral groove. Both phases emerge and are directed downward through the channel 130 towards the bottom 160 of the separator. At this point the liquid continues downward by momentum while the fully expanded vapor reverses direction and exhausts out the open top of tube 170. For safely, the use of an open container 170 presumes the container is located in a well ventilated compartment such as a fume hood to prevent exposure to the escaping vapors. It should be noted that the relative position of separator 150 to collection tube 170 in FIG. 3 is only exemplary. It needs to be lowered only as far as necessary to direct the liquid droplets into tube 170. In some cases this will be at a position fully above the tube making venting of the gas even less restrictive and allowing maximum use of the container volume for collected liquid.

Other embodiments for a parallel collection device using a gas-liquid separator assembly are illustrated in FIG. 4. In these embodiments, SFC system 200 delivers a flowstream to BPR 210. A biphasic aerosolized mobile phase consisting of expanding CO2 gas, organic modifier liquid, and occasional dissolved components flows out of BPR 210. Expanding flow continues from BPR 210 to valve 220, where it is typically directed along flow path 240 to waste. When or after components of interest in the flowstream are detected by a detector in SFC system 200; valve 220 is activated. When valve 220 is activated, the flowstream can be directed away from waste line 240 to line 230 and into parallel separator 270. Parallel separator 270 is comprised of separator assembly 150, collection container 260, lid 250 which comprises a pressure-resistant seal, and vent tube 280. Optional filter elements 290 can be placed into vent line 280 to ensure that little or no aerosol escapes from the collection container 260 to vent 280. After the gas-liquid mixture enters separator 270, the mobile phase is separated by separator assembly 150. Liquid droplets 252 are allowed to drain or to be forced to the bottom of container 260 and collect as liquid fractions 254, while gas or vapor components are pneumatically forced out of the container 260 through vent line 280. While separator 270 is described as comprising the collection container 260 which is used to accumulate the desired liquid fraction 254, one skilled in the art will recognize that collection container 260 may either act as a final collection point or instead be designed as an intermediate drain prior to a final storage of the accumulated liquid in a remote or different container without departing from the scope or spirit of the invention. Further, valve 220 may be replicated at multiple points along waste line 240 to allow addition of multiple separators 270 to operate in parallel in the flow system. An alternative implementation of FIG. 4 would make lid 250, vent line 280 and filter 290 optional and use container 260 as an open container in a manner similar to FIG. 3. The use of such an open container presumes the container is located in a well ventilated compartment such as a fume hood to prevent exposure to the escaping vapors.

Figure 5:
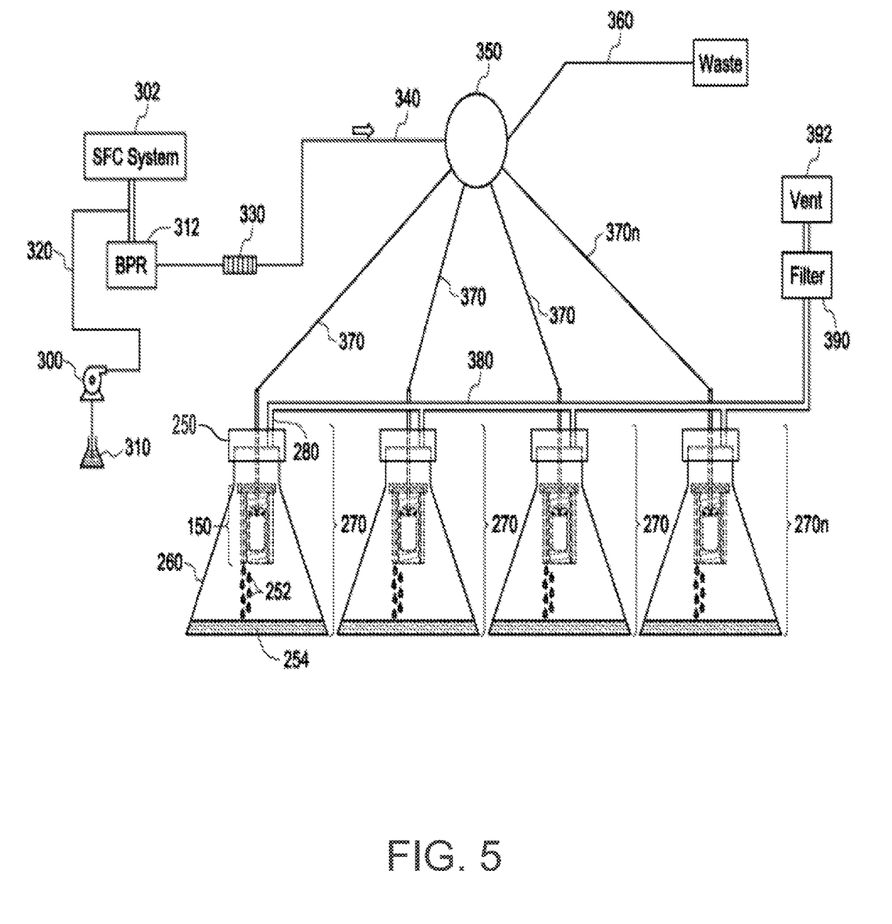
FIG. 5 illustrates an embodiment of a parallel separator system using a preferred filter assembly.

Additional embodiments of a parallel gas-liquid separation system are illustrated in FIG. 5. SFC system 302 delivers a biphasic mobile phase comprising expanding $CO_2$ gas, and an organic modifier, and occasional dissolved components out of BPR 312. Expanding flow continues from BPR 312 to valve 350, where it is typically directed along flow path 360 to waste. When or after components of interest in the flowstream are detected by a detector in SFC system 302, valve 350 is activated. When or after valve 350 is activated, the flowstream can be directed away from waste line 360 and into one or more of flow paths 370 to 370n leading to one or more parallel separators 270 to 270n. Each parallel separator 270 is comprised of separator assembly 150, collection container 260, lid 250 which comprises a pressure-resistant seal, and vent tube 280. Optional filter elements 390 can be placed into manifold vent line 380 to ensure that little or no aerosol escapes from the collection containers 260 to vent 392. After the gas-liquid mixture enters each separator 270, the mobile phase is separated by a respective separator assembly 150. Liquid droplets 252 are allowed to fall by gravity to the bottom of container 260 and collect as liquid fractions 254, while vapor components are pneumatically forced out of the container through vent line 380. Separator 270 contains the collection container 260 used to accumulate the desired liquid fraction 254. One skilled in the art will recognize that collection container 260 may either act as a final collection point or instead be designed as an intermediate drain prior to a final storage of the accumulated liquid to a remote or different container without departing from the scope or spirit of the invention. As with FIG. 4, separators 270n may also be open containers vented via an appropriate surrounding enclosure.

Several features that can improve the overall robustness of the collection process are shown in the functional flow diagram of FIG. 8. Additionally, as shown in FIG. 5, an optional solvent pump 300, supplied by reservoir 310 is used to provide a minimum solvent flow to the parallel separators 270n. This ensures sufficient liquid phase to maintain a regular drainage flow from assembly 150n. The flow is introduced via flow line 320, which can be teed into the flow system either before or after the BPR 312. If $CO_2$ is used as a compressible fluid source, then optional heating assembly 330 is used to restore heat to the flow path 340 that is lost due to the evaporation of $CO_2$ within the flow line. Flow path 340 delivers the gas-liquid mixture to selection valve 350, which is used to direct the flow to one of multiple separators 270n. In one embodiment, one or more separators 270n in the flow path may be designated to collect only waste while other separators are designated to collect the liquid fractions 254. A common vent 392 via manifold path 380 may be used for all separators 270n in the system, or alternatively, each individual separator 270 to 270n could be vented separately from the others.

Figure 6:
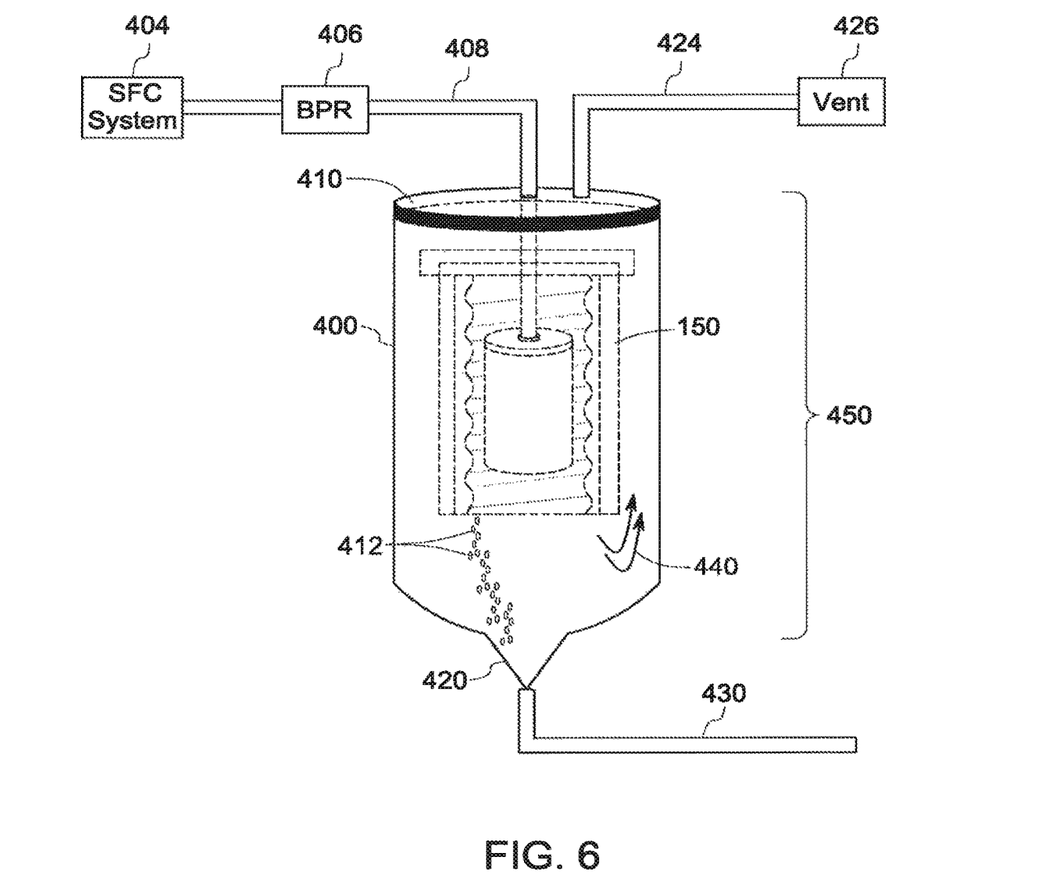
FIG. 6 illustrates an embodiment of a series separator system using a preferred filter assembly.

FIG. 6 illustrates a more detailed view of a series gas-liquid separator 450 used for fraction collection. SFC system 404 delivers a biphasic mobile phase consisting of pressurized $CO_2$, and an organic modifier, and occasional dissolved components out of BPR 406 via flow path 408. As the mobile phase passes through BPR 406, it begins expanding. Flow continues from BPR 406 to flow path 408 and into separator 450. As illustrated in the figure, separator 450 is comprised of separation assembly 150, separator housing container 400, sealing lid 410, drainage port 420 and drainage transfer line 430. Separator 450 is designed to receive a continuous gas-liquid stream from a flowstream that passes through backpressure regulator 406 and subsequently to separate the gas/vapor from the liquid in the flowstream. Separator 450 vents the gas flow via an annular space between assembly 150 and collection container 400, as shown by arrow 440. Gas 440 rises into flow path 424 to reach vent 426. Liquid fractions 412 drain through the annular space by gravity through port 420 and continue to drain through line 430 to a collection container or to an additional separation or collection system. As an alternative to gravity flow of liquid through and pneumatic flow of gas to the vent line 424, negative pressure could be applied to draw one or each flowstream away from separator 450.

Figure 7:
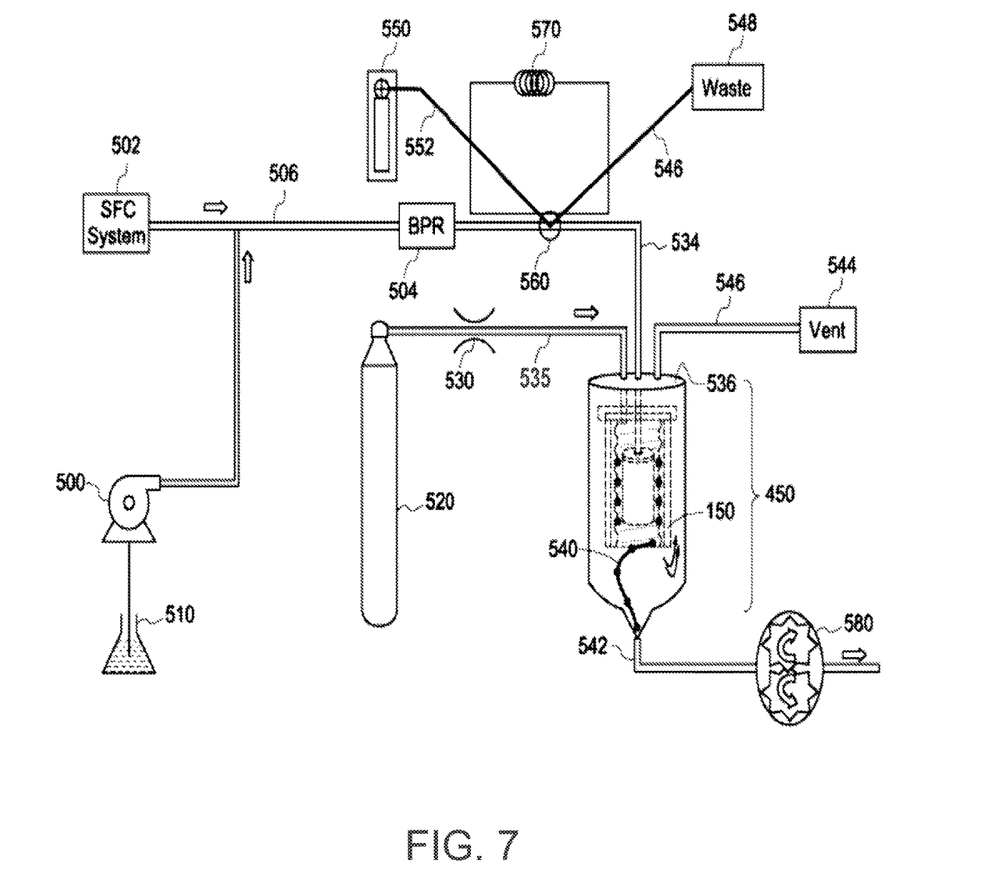
FIG. 7 illustrates an embodiment of a series separator using a preferred filter assembly.

FIG. 7 illustrates alternative embodiments of a series gas-liquid separator comprising various combinations of system components. As one skilled in the art will recognize, these alternatives could also be applied to a parallel system such as described relating to the system in FIG. 5. SFC system 502 delivers a biphasic mobile phase consisting of pressurized $CO_2$, and an organic modifier, and occasional dissolved components from BPR 504 via flow path 506. Expanding flow continues from BPR 504 to flow path 534 and into separator 450. Pump 500 draws solvent liquid of relatively low compressibility from reservoir 510, which represents an optional make-up pump assembly. For the series separator 450, it is preferable to ensure that minimum liquid solvent stream is maintained to account for evaporation and provide a relatively short drain time from within separator assembly 150. Optional gas cylinder 520 with restrictor 530 in the transfer line 535 can be used to ensure that a vapor "down draft" is maintained at the top to the spiral channel 130 (FIGS. 2 and 3) of assembly 150 so that liquid droplets may not accumulate high in the spiral channel 130. Optional drip line 540 is used to provide a direct drainage path for liquid droplets emerging from the spiral channel 130 to a drainage port and associated drainage transfer line 542. The drip line 540 can be fabricated from polymer filaments or inert metal wires, although the more wettable metallic wires tend to provide a better cohesive channel for the drops to follow. The top of the collection chamber of the separator 450 may be closed by a sealing lid 536 configured to accommodate the transfer lines 534 and 535 as well as a vent line 524 leading to a vent 544.

Other embodiments provide additional rinsing capabilities via syringe pump 550 connected by flow path 552 to injection valve 560 and loop 570. In its normal state, the loop 570 is connected between the syringe pump 550 and waste 548 via flow path 546, where loop 570 can be filled with appropriate wash solvent. When the end of a peak is detected, the valve 560 is switched to deliver the loop 570 contents to separator assembly 150 as a deluge wash step. This action should sufficiently limit any residual carryover from the prior sample. After a short time the valve 560 is switched back and the loop is refilled. It can be appreciated that pump 550 could be replaced by a variety of other pump types or even a pressurized wash solvent container and solenoid valve to accomplish the loop filling.

A further embodiment in FIG. 7 comprises an active drain pumping system which is the subject of a separate pending patent application that is assigned to the same assignee of the present application. Pump 580 represents a low internal volume pump which actively draws liquid and a small amount of vapor from separator 450 via the drainage port and associated drainage transfer line 542. The presence of the pump 580 allows the separator 450 to perform well with a multitude of liquid viscosities and flow ranges without being concerned regarding the passive restriction of the collection flow line at the exit of the pump 580.

Advantages of the embodiments are numerous. Both vapor or gas and liquid are directed downward in the separator which improves the liquid drainage time while allowing the vapor to fully expand before moving upward to the exhaust exit. Vapor is directed pneumatically to a vent that is positioned away from the liquid drainage region. Liquid is directed by gravity and pneumatic forces to the bottom of the separator for collection or where an optional drain port may carry the fluid to a remote container. The self-cleaning, low pressure drainage path may be used for large or small volume liquid accumulation. Additionally, the collector does not require the prior art of a heating step or collection container pressurization for the removal of aerosols, however, auxiliary heating can be used as means to reduce external condensation and freezing on the exterior of the separator and transfer lines.

Many modifications and variations can be possible in view of the above teachings. The embodiments were chosen and described to explain the principles of the disclosure and their practical applications, and to enable others skilled in the art to best utilize the disclosure and various embodiments with various modifications as suited to the particular use contemplated.

While this specification contains many specifics, these should not be construed as limitations on the scope of what is being claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. An apparatus for a gas-liquid flowstream, comprising:
a constraint housing having an upper end and a lower end, and being configured for receiving a pressurized gas-liquid or aerosolized flowstream for forming within the constraint housing coalesced droplets as the gas-liquid flowstream passes therethrough to thereby separate the gas-liquid flowstream into a gas phase and a liquid phase;
wherein the lower end of the constraint housing has an opening to allow at least a portion of the separated gas phase to exit the constraint housing and thereby improve a drainage time of the liquid phase; and
a drip line connected to an exit of the opening in the lower end of the constraint housing and providing a path for direct drainage of the liquid phase from the constraint housing, and the drip line is configured for release of liquid phase droplets from the apparatus.

2. The apparatus of claim 1, wherein the constraint housing comprises a channel for collection of the liquid phase, and the drip line is connected to an open portion of the channel.

3. The apparatus of claim 2, wherein the channel comprises a spiral channel.

4. The apparatus of claim 1 further comprising:
a coalescence filter disposed inside the constraint housing; and
an inlet flowpath having fluidic communication with an interior cavity of the filter.

5. The apparatus of claim 4, wherein at least a portion of the filter has an external surface area relatively larger than a cross-sectional area of said inlet flowpath to the filter.

6. The apparatus of claim 4, wherein the filter is shaped as one of a cylinder, a sphere, a cuboid, a prism, or a trapezoid.

7. The apparatus of claim 1, further comprising:
a coalescence filter disposed inside the constraint housing; and
the drip line drains liquid separated from said filter.

8. The apparatus of claim 1, wherein the lower end of the constraint housing comprises a tapered portion, and the drip line is coupled to the tapered portion.

9. The apparatus of claim 1, wherein the drip line comprises a fabrication of polymer filaments or inert metal wires, and the liquid droplets are drained along an exterior surface of the drip line.

10. A gas-liquid separation system, comprising:
the apparatus of claim 1, wherein the constraint housing comprises an inlet flowpath that receives the pressurized gas-liquid or aerosolized flowstream; and
a vent.

11. The system of claim 10, wherein the drip line collects the liquid phase and the vent collects the gas component.

12. The system of claim 10, further comprising:
a make-up pump which draws solvent liquid from a reservoir and pumps the liquid into the pressurized gas-liquid flowstream prior to entering said inlet flowpath.

13. The system of claim 10, further comprising:
a pressurized gas source which provides a gas flow to a channel for collection of the liquid phase, wherein said gas flow provides a downdraft to force liquid out of the channel.

14. The system of claim 10, further comprising:
a pressurized rinse assembly connected by a valve or pump to the inlet flowpath of the constraint housing, wherein the rinse assembly provides a wash solvent into said inlet flowpath thereby providing a wash to the constraint housing.

15. The system of claim 10, further comprising:
a coalescence filter inserted in the constraint housing;
a channel disposed between the coalescence filter and the constraint housing, the channel configured for receiving the gas-liquid flowstream after the flowstream passes through the coalescence filter,
wherein the drip line is connected to an open portion of the channel.

16. The system of claim 10, wherein
the constraint housing comprises a channel for collection of the liquid fraction, and the system further comprises a gas supply line for providing a gas to the channel.

17. The system of claim 10, further comprising a pump coupled to the lower end of the constraint housing.

\* \* \* \* \*